United States Patent [19]

Rokach et al.

[11] 4,075,225

[45] Feb. 21, 1978

[54] PYRROLO[2,1-B][3]BENZAZEPINES

[75] Inventors: Joshua Rokach, Laval; Joseph G. Atkinson, Montreal, both of Canada; Clarence S. Rooney, Worcester, Pa.

[73] Assignee: Merck & Co., Inc., Rahway, N.J.

[21] Appl. No.: 701,047

[22] Filed: June 29, 1976

[51] Int. Cl.² .......................................... C07D 487/04
[52] U.S. Cl. ..................... 260/326.31; 260/326.5 B; 260/326.47; 260/326.5 S; 260/326.5 J; 260/326.5 SF
[58] Field of Search ................ 260/326.5 B, 326.5 S, 260/326.5 SF, 326.31

[56] References Cited
PUBLICATIONS

Cooper et al., Tet. Letters, 45, 4321–4324, (1971).
Huiggen et al., Chem. Ber. 93, 65–81, (1960).
Weinskin, J. Org. Chem., 41, 875, (1976).

*Primary Examiner*—Donald G. Daus
*Assistant Examiner*—Mark L. Berch
*Attorney, Agent, or Firm*—William H. Nicholson; Harry E. Westlake, Jr.

[57] ABSTRACT 6,11-Dihydro-5H-Pyrrolo[2,1-b][3]benzazepin-11-one and derivatives thereof are generally prepared by Friedel-Crafts ring closure of a N-phenethylpyrrole-2-carboxylic acid halide. They are useful intermediates in the synthesis of skeletal muscle relaxants and tranquilizers such as 11-(3-dimethylaminopropylidene)-6,11-dihydro-5H-pyrrolo[2,1-b][3]benzazepine.

18 Claims, No Drawings

PYRROLO[2,1-B][3]BENZAZEPINES

BACKGROUND OF THE INVENTION

Over the past several years several so-called tricyclic compounds such as amitriptyline, cyclobenzaprine, nortriptyline and protriptyline have gained importance as centrally acting pharmacological agents. Now with the present invention, there is provided compounds from which new tricyclic compounds can be prepared which have skeletal muscle relaxant and tranquilizer activity.

Thus, it is an object of the present invention to provide compounds of structural formula:

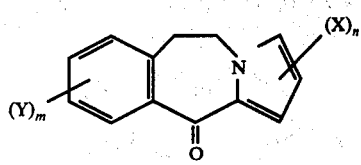

It is a further object to provide processes for the preparation of the compounds.

DETAILED DESCRIPTION OF THE INVENTION

In particular, this invention relates to compounds of structural formula:

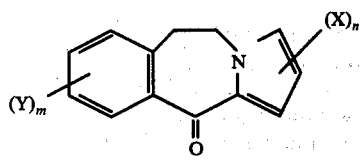

wherein
$n$ is 3, 2, 1, or 0 (X is hydrogen); $m$ is 4, 3, 2, 1 or 0 (Y is hydrogen); and X and Y are independently selected from
(1) hydrogen,
(2) halo, such as chloro, bromo, fluoro, or iodo,
(3) formyl,
(4) lower alkanoyl, especially $C_{2-6}$ alkanoyl such as acetyl, pentanoyl, or 2-methylpropanoyl,
(5) lower alkyl, especially $C_{1-5}$ alkyl, either straight or branched chain, such as methyl, propyl, or pentyl,
(6) lower alkoxycarbonyl, especially ($C_{1-5}$ alkoxy)-carbonyl,
(7) hydroxy-lower alkyl, especially hydroxy-$C_{1-3}$-alkyl,
(8) perhalo-lower alkyl, especially perhalo-$C_{1-13}$-alkyl, such as trifluoromethyl,
(9) lower alkoxy, especially $C_{1-3}$ alkoxy, such as methoxy or propoxy,
(10) cyano,
(11) perhalo-lower alkylthio, especially perhalo-$C_{1-3}$ alkylthio, such as trifluoromethylthio,
(12) lower alkylthio, especially $C_{1-3}$ alkylthio, such as methylthio or propylthio,
(13) lower alkylsulfonyl, especially $C_{1-3}$ alkyl sulfonyl, such as methylsulfonyl or isopropylsulfonyl,
(14) perhalo-lower alkylsulfonyl, especially perhalo-$C_{1-3}$ alkylsulfonyl, such as trifluoromethyl sulfonyl,
(15) lower alkylsulfinyl, especially $C_{1-3}$ alkylsulfinyl, such as methylsulfinyl,
(16) perhalo-alkylsulfinyl, especially perhalo-$C_{1-3}$ alkylsulfinyl, such as trifluoromethylsulfinyl,
(17) amino,
(18) lower alkanoylamino, especially $C_{2-6}$ alkanoylamino, such as acetylamino, or pentanoylamino,
(19) lower alkylamino, especially $C_{1-3}$ alkylamino,
(20) di(lower alkyl)amino, especially di($C_{1-3}$ alkyl)-amino,
(21) hydroxy,
(22) N-lower alkylcarbamoyl, especially N-$C_{1-3}$ alkylcarbamoyl,
(23) N,N-di(lower alkyl)carbamoyl, especially N,N-di($C_{1-3}$ alkyl)carbamoyl,
(24) nitro,
(25) di(lower alkyl)sulfamoyl, especially di($C_{1-3}$-alkyl)-sulfamoyl,
(26) lower alkoxycarbonylamino, especially $C_{1-3}$ alkoxycarbonylamino,
(27) N-loweralkyl-carbamoyloxy, especially $C_{1-3}$ alkylcarbamoyloxy,
(28) carboxy, or
(29) carbamoyl.

One embodiment of the novel compounds of this invention is that wherein the X substituents are in the 2 and/or 3 position and $n$ is 2, 1, or 0 (X is hydrogen). Another embodiment of the novel compounds is that wherein $m$ and $n$ are independently 1 or 0.

A preferred embodiment of the novel compounds of this invention is the compound of structural formula:

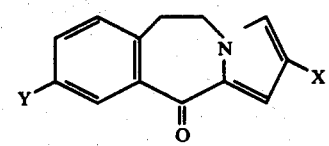

A still more preferred embodiment of the novel compounds is where one of X and Y is hydrogen, and the other is hydrogen, cyano, formyl, or $C_{2-6}$ alkanoyl.

The novel compounds of the present invention are generally prepared by a Friedel-Crafts reaction wherein the catalyst is preferably aluminum chloride and the starting material is a N-phenethylpyrrole-2-carboxylic acid halide, preferably the chloride. The process comprises mixing a N-phenethylpyrrole-2-carboxylic acid halide and a Friedel-Crafts catalyst in a halo hydrocarbon solvent such as 1,1,2,2-tetrachloroethane or dichloromethane or nitromethane or the like at −20° C. to 150° C. for from 1 minute to about 5 hours.

The above process of ring closure to the novel ketones of this invention proceeds with difficulty because of side reactions in those cases wherein the pyrrole ring is unsubstituted or substituted with activating substituents. In such cases it is convenient to halogenate, especially brominate, the intermediate pyrrole carboxylic acids to the 3,4,5-, 4,5 or 4-halo-pyrrole carboxylic acids, ring close via the acid chloride as described above, and then if desired, dehalogenate. The dehalogenation is accomplished by hydrogenolysis in a solvent such as a lower alkanol, in the presence of an acid acceptor, such as a tertiary amine, and a noble metal catalyst such as palladium until the required amount of hydrogen is consumed.

Alternatively, in those cases wherein the pyrrole ring is unsubstituted and/or the benzene ring is substituted with a deactivating group such as nitro or iodo, it is convenient to start with a 2-(2-pyrrol-1-yl)ethylbenzoic acid and ring close to the desired ketone in polyphosphate ester at 10°–50° C. for 1–30 hours.

The nitro-ketones produced as described above, as well as being a novel compound of this invention, are useful intermediates to the corresponding amino-ketones, acylamino-ketones, and alkyl- and dialkyl-amino-ketones prepared by art recognized procedures.

Similarly, the iodo-ketone produced as described above is a useful intermediate for preparing such as the trifluoromethylthio, and methylthio-ketones by art recognized procedures.

The novel compounds, wherein the substituent X is 2-acyl, such as acetyl, dimethylsulfamoyl, or the like, are prepared by an alternate procedure involving acylation of a novel compound of this invention unsubstituted in the pyrrole ring with the appropriate acid chloride such as acetyl chloride, dimethylsulfamoyl chloride, or the like in the presence of a Friedel-Crafts catalyst such as aluminum chloride in an inert solvent such as methylene chloride, 1,1,2,2-tetrachlorethane, nitromethane or the like at −20° C. to 150° C. for 5 minutes to about 3 hours.

The alkanoyl derivatives described above may also be prepared by treating the ketone with an excess of alkanoyl chloride without the Friedel-Crafts catalyst and without the inert solvent at reflux temperature. A mixture of the 2-, and 3-alkanoyl ketones are obtained which are separated by chromatography on silica gel to provide the 3-alkanoyl compounds.

Formyl-6,11-dihydro-5H-pyrrolo[2,1-b][3]benzazepin-11-ones may be prepared by reduction of the corresponding cyano compound with nickel-aluminum alloy in formic acid or aqueous formic acid at from 50° C. to reflux temperature for 30 minutes to 5 hours.

The carbamoyl substituted ketones may be prepared by hydrolysis of cyano ketones with a strong mineral acid such as hydrochloric acid in acetic acid at 50° C. to reflux temperature for 1-5 hours.

Carboxy-ketones may be prepared by diazotization of the corresponding carbamoyl-ketones with sodium nitrite in a strong mineral acid, such as aqueous sulfuric acid.

Alkyl-, and di(alkyl)carbamoyl ketones may be prepared from the corresponding carboxy ketones by forming the acid chloride therefrom followed by treatment with an alkylamine or a di(alkyl)amine in an inert organic solvent such as methylene chloride or the like, at −20° C. to reflux temperature until the reaction is complete.

Alkoxycarbonyl ketones may be prepared by heating at 50° C. to reflux for 1-8 hours the corresponding carboxy ketone in a lower alkanol in the presence of a strong mineral acid, such as hydrogen chloride.

2- and 3- Trifluoromethylthio-ketones may be prepared by treating a ketone unsubstituted in the pyrrole ring with trifluoromethylsulfenyl chloride in a chlorinated hydrocarbon, such as chloroform or the like, at −10° C. to 50° C. for 1-6 hours, followed by chromatographic separation on an adsorbent such as silica gel.

1- and 3-Trifluoromethyl ketones may be prepared by treating a ketone unsubstituted in the pyrrole ring with trifluoromethyliodide in an inert organic solvent such as acetonitrile in the presence of an acid acceptor such as a tertiary amine, for example pyridine at 10°-50° C. under the influence of irradiation with U.V. light for 10-24 hours. The 1- and 3-isomers are subsequently separated by chromatography on an absorbent such as silica gel.

Novel compounds with a trifluoromethylthio substituent in the benzo ring may be prepared by reacting the corresponding iodo- or bromo- ketone with trifluoromethylthiocopper formed by the reaction of copper powder with bis(trifluoromethylthio)mercury in a polar organic solvent such as dimethylformamide, quinoline, or hexamethylphosphoramide at 50° C. to 200° C. for 0.5-24 hours.

Similarly, cyano ketones may be prepared by treating the bromo- or iodo-ketones with cuprous cyanide.

The trifluoromethylthio and alkylthio compounds are converted to the corresponding sulfinyl- and sulfonylketones with hydrogen peroxide.

The novel compounds of this invention are useful intermediates for the synthesis of skeletal muscle relaxants and tranquilizers of structural formula:

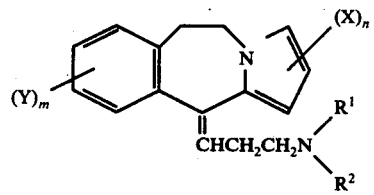

wherein X, Y, $m$, and $n$ are as previously defined and $R^1$ and $R^2$ are independently selected from hydrogen, lower alkyl, or alkenyl which may be straight chain, branched chain, or cyclic, or may be joined together to form groups such as 1-piperidyl, 1-pyrrolidyl or 4-morpholinyl.

The skeletal muscle relaxants preparable from the novel compounds of this invention are administered in the usual pharmaceutical unit dosage forms, preferably orally at the rate of 0.1 to 30 mg./kg. of body weight per day. For tranquilizer utility the dose range is 0.1 to 30 mg./kg. of body weight per day.

The pharmacologically active compounds are preparable from the novel compounds of this invention in accordance with the following chemical equation which is exemplified by the synthesis of 6,11-dihydro-11-(3-dimethylaminopropylidene)-5H-pyrrolo[2,1-b][3]benzazepine.

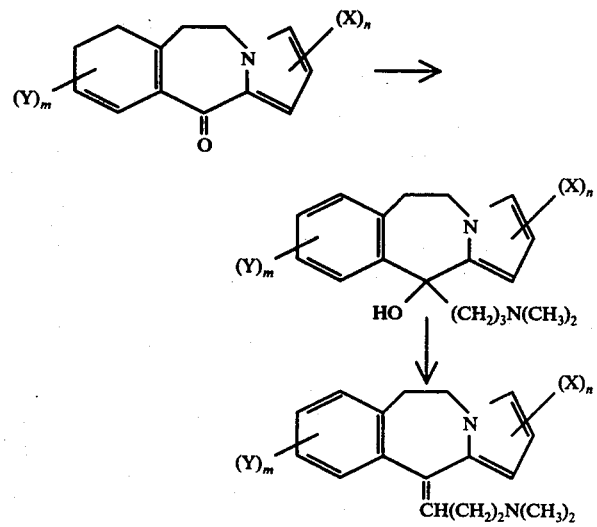

Preparation of 6,11-dihydro-11-(3-dimethylaminopropylidene)-5H-pyrrolo[2,1-b][3]benzazepine Step A: Grignard Reaction To a solution of 16 g. (0.081 mole) of 6,11-dihydro-5H-pyrrolo[2,1-b][3]benzazepin-11-one in 300 ml. tetrahydrofuran (THF) is added 150 ml. of 1.0 N 3-dimethylaminopropyl magnesium chloride. After stirring for 40 minutes at ice-bath temperature and for 1.5 hours at 25° C., the bulk of the solvent is distilled below 45° C. under reduced pressure. The residue is dissolved in 500 ml. of methylene chloride and the Grignard adduct is hydrolyzed by the dropwise addition of 15 ml. water with cooling in an ice bath. The methylene chloride solution is decanted and the gelatinous precipitate is extracted three times with 80 ml. portions of boiling benzene. The combined organic extracts are washed with water and then evaporated under reduced pressure to yield, after crystallization from ethanol, 11-hydroxy-11-(3-dimethylaminopropyl)-6,11-dihydro-5H-pyrrolo-[2,1-b][3]benzazepine, m.p. 68°-70°.

Step B: Dehydration

Hydrogen chloride gas is bubbled through a solution of 4.8 gm. (0.017 moles) of 11-hydroxy-11-(3-dimethylaminopropyl)-6,11-dihydro-5H-pyrrolo[2,1-b][3]benzazepine in 70 ml. of chloroform at 0° C. for 5 minutes. The resulting dark mixture is stirred for an additional 5 minutes, and then washed with 6M NaOH to provide, after evaporation of the chloroform, 4.3 g. of 11-(3-dimethylaminopropylidene)-6,11-dihydro-5H-pyrrolo[2,1-b][3]benzazepine as an oil. It is converted to a crystalline oxalate by adding a solution of 266 mg. of the free base in 5 ml. of ethanol to a mixture of 90 mg. of oxalic acid and 2 ml. of ethanol and collecting the precipitate by filtration and air drying; m.p. 140°-165° C. (dec.).

The methods of synthesis and use of the skeletal muscle relaxants is more fully described and claimed by Rokach et al. in concurrently filed U.S. Patent Application Ser. No. 701,001, which is a continuation-in-part of U.S. Ser. No. 592,436, filed July 2, 1975 now abandoned.

The following examples representatively illustrate but do not limit the product, or process aspects of the present invention.

EXAMPLE 1

6,11-Dihydro-5H-pyrrolo[2,1-b][3]benzazepin-11-one

Step A: Preparation of 1-(2-phenethyl)-pyrrole-2-carboxylic acid and 1-(2-phenethyl)-4-cyanopyrrole-2-carboxylic acid Method A: Preparation of 1-(2-phenethyl)pyrrole-2-carboxylic acid Methyl pyrrole-2-carboxylate (10.0 g.) in 100 ml. dimethylformamide (DMF) was treated portionwise with sodium hydride (2.21 g.) at 25° C. After evolution of hydrogen ceased, styrene oxide (11.52 g.) was added and the mixture was heated at 115° C. for 1 hour. The resulting mixture was poured into 600 ml. ice-water and extracted with ether (2 × 100 ml.). The aqueous phase was acidified to pH 1 with 6N HCl to precipitate the product, which was collected by filtration, washed with water and dried, m.p. 183°-185° C.

The unsaturated acid, trans-1-styrylpyrrole-2-carboxylic acid, 24.4 g. was suspended in 200 ml. ethanol in the presence of 1 g. 10% Pd/C and hydrogenated under 3 atmospheres hydrogen until uptake of hydrogen ceased. After removal of the catalyst by filtration, the product, 1-(2-phenethyl)-pyrrole-2-carboxylic acid was obtained by evaporation of solvent, m.p. 124°-125° C.

Method B: Preparation of 1-(2-phenethyl)-4-cyanopyrrole-2-carboxylic acid

To 75 g. of potassium carbonate in 300 ml. of dimethylformamide was added successively 84 g. of 2-phenethyl bromide and 63.5 g. of 2-carbomethoxy-4-cyano-pyrrole. The mixture was heated in an oil bath at 85° C. for 4 hours, poured into 1000 ml. of water, and extracted with 3 × 1000 ml. of ether. The combined organic extracts were washed with 2 × 100 ml. of water, dried over magnesium sulfate, filtered and evaporated. The residue was triturated with 500 ml. of fresh ether and the resulting solid was filtered to yield 82.8 gm. (77%) of 1-(2-phenethyl)-2-carbomethoxy-4-cyanopyrrole, m.p. 109°-110° C.

A mixture of 80.3 g. of 1-(2-phenethyl)-2-carbomethoxy-4-cyanopyrrole, 23.3 g. of potassium hydroxide and 900 ml. of ethanol was heated at 75° C. for 2 hours. The solution was evaporated to dryness, the residue was dissolved in 1000 ml. of water, and the solution was acidified to pH 1 with 6N HCl to cause precipitation of 1-(2-phenethyl)-4-cyanopyrrole-2-carboxylic acid. The product was collected by filtration, washed with water and dried to give 72 g. (95%), m.p. 195°-195.5° C.

Following the procedure described in Example 1, Step A, the nuclear substituted 1-(2-phenethyl)-pyrrole-2-carboxylic acids (A) of Table I are obtained when the indicated molar equivalent substitutions for the styrene oxide (B) or 2-(phenethyl) halide (D) and the methyl-pyrrole-2-carboxylate (C) of Example 1 are made:

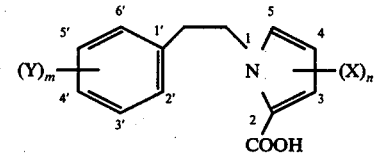

A

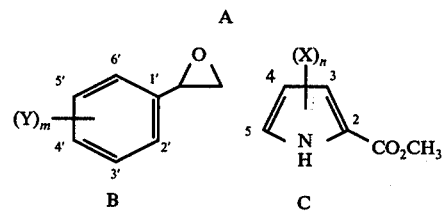

B      C

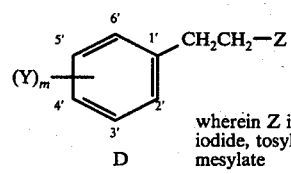

wherein Z is bromide, iodide, tosylate or mesylate

D

TABLE I

| COMPOUND | PHENYL REACTANT $(Y)_m$ | B or D | PYRROLE REACTANT, C $(X)_n$ | PRODUCT, A $(Y)_m$ | $(X)_n$ | M.P. (° C.) |
|---|---|---|---|---|---|---|
| 1. | H | (B) | 4-SO$_2$N(CH$_3$)$_2$ | | 4-SO$_2$N(CH$_3$)$_2$ | |
| 2. | H | (B) | 4-SO$_2$CH$_3$ | | 4-SO$_2$CH$_3$ | |
| 3. | H | (B) | 4-SO$_2$CH(CH$_3$)$_2$ | | 4-SO$_2$CH(CH$_3$)$_2$ | |
| 4. | H | (B) | 4-SO$_2$CF$_3$ | | 4-SO$_2$CF$_3$ | |

TABLE I-continued

| COMPOUND | PHENYL REACTANT $(Y)_m$ | B or D | PYRROLE REACTANT, C $(X)_n$ | PRODUCT, A $(Y)_m$ $(X)_n$ | M.P. (° C.) |
|---|---|---|---|---|---|
| 5. | H | (D) | 4-CN | 4-CN | 195–195.5 |
| 6. | H | (B) | 4-COOC$_2$H$_5$ | 4-COOC$_2$H$_5$ | |
| 7. | H | (D) | 4-NO$_2$ | 4-NO$_2$ | |
| 8. | H | (B) | 4-COCH$_3$ | 4-COCH$_3$ | |
| 9. | H | (B) | 4-CF$_3$ | 4-CF$_3$ | |
| 10. | 4'-O—C(=O)—NHCH$_3$ | (B) | H | 4'-OCONHCH$_3$ | |
| 11. | 4'-NH—COOCH$_3$ | (B) | H | 4'-NHCOOCH$_3$ | |
| 12. | 4'-CH$_3$ | (B) | H | 4'-CH$_3$ | |
| 13. | H | (D) | 4,5-Br$_2$ | 4,5-Br$_2$ | 178–179 |
| 14. | H | (D) | 4-Br | 4-Br | |
| 15. | H | (D) | 4-Cl | 4-Cl | 117–120 |
| 16. | H | (D) | 5-CN | 5-CN | |
| 17. | H | (D) | 3,4,5-Br$_3$ | 3,4,5-Br$_3$ | 182–184 |
| 18. | H | (B) | 4-SCF$_3$ | 4-SCF$_3$ | 123–125 |
| 19. | H | (B) | 4-CON(CH$_3$)$_2$ | 4-CON(CH$_3$)$_2$ | |
| 20. | H | (D) | 4-CH$_3$—3,5-Br$_2$ | 4-CH$_3$—3,5-Br$_2$ | |
| 21. | 4'-NH—COCH$_3$ | (D) | 3,4,5-Br$_3$ | 4'-NHCOCH$_3$—3,4,5-Br$_3$ | |
| 22. | H | (D) | 4-CHO | 4-CHO | |
| 23. | 4'-CH(CH$_3$)$_2$ | (D) | H | 4'-CH(CH$_3$)$_2$ | |
| 24. | 4'-SCH$_3$ | (D) | H | 4'-SCH$_3$ | |
| 25. | 3',4'-(CH$_3$)$_2$ | (D) | 4-CN | 3',4'-(CH$_3$)$_2$—4-CN | |
| 26. | 4'-OH | (D) | 4-CN | 4'-OH—4-CN | |
| 27. | 4'-OCH$_3$ | (D) | 4-CN | 4'-OCH$_3$—4-CN | |

Step B: Preparation of 1-(2-phenethyl-2,3-dibromopyrrole-5-carboxylic acid chloride To a solution of 1-(2-phenethyl)pyrrole-2-carboxylic acid (105 g., 0.49 mole) in acetic acid (750 ml.) was added 156 g. of bromine over 30 minutes at 25° C. Formic acid (100 ml.) was added and the reaction chilled in ice, to yield 66 gm. (0.18 moles) of 1-(2-phenethyl)-2,3-dibromopyrrole-5-carboxylic acid after solvent removal. Heating the resulting acid in excess thionyl chloride for 1 hour yielded the acid chloride in near quantitative yield after removal of solvent by evaporation, washing with petroleum ether and drying in vacuum.

Following the procedure of Example 1, Step B, but using chlorine in place of bromine, there is obtained 1-(2-phenethyl)-2,3-dichloro-5-pyrrole carboxylic acid chloride.

Following the procedure of Example 1, Step B, the mono- and dibrominated acid chlorides depicted in Table II are obtained when an equivalent amount of the appropriate free acid from Table I replaces the 1-(2-phenethyl)-pyrrole-2-carboxylic acid used in Example 1, Step B, and either 1 or 2 equivalents of bromine is reacted therewith.

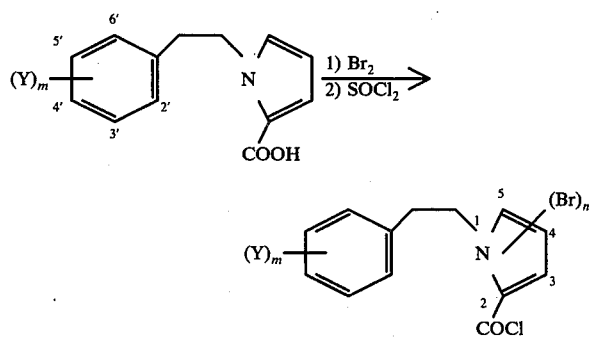

TABLE II

| Starting material from | $(Y)_m$ | Equivalents of Bromine | $(Br)_n$ |
|---|---|---|---|
| Example 1A | H | 1 | 4-Br |
| Table I(12) | 4'-CH$_3$ | 2 | 4,5-Br$_2$ |
| Table I(10) | 4'-OCONHCH$_3$ | 2 | 4,5-Br$_2$ |
| Table I(11) | 4'-NHCOOCH$_3$ | 2 | 4,5-Br$_2$ |
| Table I(24) | 4'-SCH$_3$ | 2 | 4,5-Br$_2$ |
| Table I(23) | 4'-CH(CH$_3$)$_2$ | 2 | 4,5-Br$_2$ |

Following the procedure of Example 1, Step B, but omitting the nuclear halogenation step, there is obtained the corresponding acid chlorides when the 1-(2-phenethyl)-pyrrole-2-carboxylic acid of Example 1, Step B, is replaced by an equivalent amount of the free acids enumerated in Table I, respectively.

Step C: Preparation of 2,3-dibromo-6,11-dihydro-5H-pyrrolo-[2,1-b][3]benzazepin-11-one To a solution of 1-(2-phenethyl)-4,5-dibromo-pyrrole-2-carboxylic acid chloride (40 g., 0.102 mole) in 800 ml. sym-tetrachloroethane at 140° C. was added 40 gm. (0.30 mole) of aluminum chloride. After three minutes, the reaction was cooled in ice, poured over 2000 g. of ice, stirred for 10 minutes, filtered, and the organic layer was separated. The aqueous layer was extracted with 2 × 200 ml. of chloroform, which was combined with the first organic layer. The combined organic solution was washed with 3 × 500 ml. of water, dried and evaporated in vacuum to provide a dark oil (29 g.) which was chromatographed on silica gel using benzene to elute in 50 ml. fractions. Fractions 5-13 were combined and evaporated to yield 20.3 gm. (0.057 moles) of 2,3-dibromo-6,11-dihydro-5H-pyrrolo-[2,1-b][3]benzazepin-11-one, m.p. 130°–132° C.

Following the procedure of Example 1, Step C, but substituting for the 1-(2-phenethyl)-4,5-dibromopyrrole-2-carboxylic acid chloride used therein an equimolecular amount of the acid chlorides prepared in accordance with Example 1, Step B, there are produced the 6,11-dihydro-5H-pyrrolo[2,1-b][3]benzazepin-11-ones described in Table III by the following process:

TABLE III

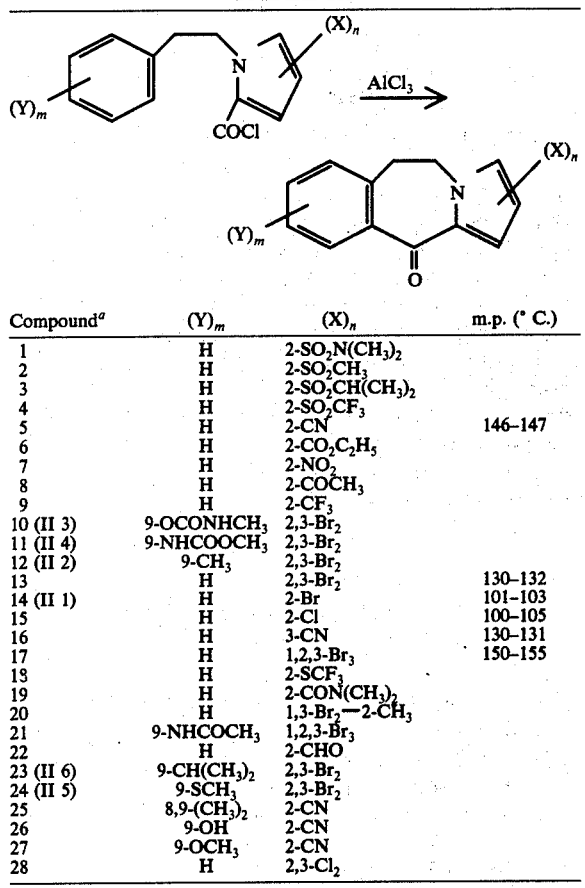

| Compound[a] | (Y)$_m$ | (X)$_n$ | m.p. (° C.) |
|---|---|---|---|
| 1 | H | 2-SO$_2$N(CH$_3$)$_2$ | |
| 2 | H | 2-SO$_2$CH$_3$ | |
| 3 | H | 2-SO$_2$CH(CH$_3$)$_2$ | |
| 4 | H | 2-SO$_2$CF$_3$ | |
| 5 | H | 2-CN | 146–147 |
| 6 | H | 2-CO$_2$C$_2$H$_5$ | |
| 7 | H | 2-NO$_2$ | |
| 8 | H | 2-COCH$_3$ | |
| 9 | H | 2-CF$_3$ | |
| 10 (II 3) | 9-OCONHCH$_3$ | 2,3-Br$_2$ | |
| 11 (II 4) | 9-NHCOOCH$_3$ | 2,3-Br$_2$ | |
| 12 (II 2) | 9-CH$_3$ | 2,3-Br$_2$ | |
| 13 | H | 2,3-Br$_2$ | 130–132 |
| 14 (II 1) | H | 2-Br | 101–103 |
| 15 | H | 2-Cl | 100–105 |
| 16 | H | 3-CN | 130–131 |
| 17 | H | 1,2,3-Br$_3$ | 150–155 |
| 18 | H | 2-SCF$_3$ | |
| 19 | H | 2-CON(CH$_3$)$_2$ | |
| 20 | H | 1,3-Br$_2$—2-CH$_3$ | |
| 21 | 9-NHCOCH$_3$ | 1,2,3-Br$_3$ | |
| 22 | H | 2-CHO | |
| 23 (II 6) | 9-CH(CH$_3$)$_2$ | 2,3-Br$_2$ | |
| 24 (II 5) | 9-SCH$_3$ | 2,3-Br$_2$ | |
| 25 | 8,9-(CH$_3$)$_2$ | 2-CN | |
| 26 | 9-OH | 2-CN | |
| 27 | 9-OCH$_3$ | 2-CN | |
| 28 | H | 2,3-Cl$_2$ | |

[a]The numbers of the compounds described in Table III correspond to the numbers of the starting materials described in Table I from which they were prepared, unless otherwise indicated. For example, compound 5 of Table III was prepared from the compound 5 of Table I. Compound 12 was prepared from compound 2 of Table II.

Step D: Preparation of 6,11-dihydro-5H-pyrrolo[2,1-b][3]-benzazepin-11-one

A suspension of 25 g. (0.070 mole) of 2,3-dibromo-6,11-dihydro-5H-pyrrolo[2,1-b][3]benzazepin-11-one in 200 ml. ethanol containing 25 ml. of triethylamine and 1 gm. of 10% Pd on charcoal was hydrogenated under 3 atmospheres of hydrogen to yield 6,11-dihydro-5H-pyrrolo-[2,1-b][3]benzazepin-11-one, m.p. 54°–55° C. after removal of catalyst, recrystallization from petroleum ether and drying under vacuum. The same compound is also obtained by hydrogenolysis of the 2,3-dichloro ketone and the 1,2,3-tribromoketone.

Following the procedure of Example 1, Step D, but substituting for the 2,3-dibromo-6,11-dihydro-5H-pyrrolo[2,1-b][3]benzazepin-11-ones used therein, an equimolecular amount of the halogenated ketones described in Table III, there are produced the ketones described in Table IV.

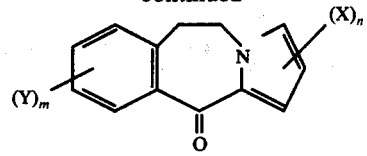

| Table | Starting Material Compound No. | (Y)$_m$ | (X)$_n$ |
|---|---|---|---|
| III | 10 | 9-OCONHCH$_3$ | H |
| III | 11 | 9-NH—COOCH$_3$ | H |
| III | 12 | 9-CH$_3$ | H |
| III | 14 | H | H |
| III | 23 | 9-CH(CH$_3$)$_2$ | H |
| III | 20 | H | 2-CH$_3$ |
| III | 21 | 9-NH—COCH$_3$ | H |
| III | 24 | 9-SCH$_3$ | H |

EXAMPLE 2

Preparation of 2-cyano-6,11-dihydro-5H-pyrrolo[2,1-b][3]-benzazepine-11-one

To a solution of 73.6 g. of 1-(2-phenethyl)-4-cyanopyrrole-2-carboxylic acid chloride in 850 ml. of tetrachloroethane maintained at 140° C. is added over a period of 2 minutes 114 g. of aluminum chloride. The resulting solution is stirred at 140° C. for 4 minutes, poured over 2000 g. of ice and the mixture stirred for 10 minutes. It is then filtered to remove insoluble tarry material and the organic layer separated. The aqueous layer is extracted with 2 × 500 ml. of chloroform, which is combined with the original organic layer, washed with 500 ml. of water and with 200 ml. portions of 1N sodium bicarbonate until the aqueous washes remain basic. The organic layer is dried over magnesium sulfate, filtered and evaporated under vacuum to leave a residue. This residue upon trituration with 300 ml. of ether readily crystallizes. The crystals are filtered and air-dried to yield 57.2 gm. (90%) of 2-cyano-6,11-dihydro-5H-pyrrolo[2,1-b][3]benzazepin-11-one, m.p. 146°–147° C.

EXAMPLE 3

Preparation of 2-formyl-6,11-dihydro-5H-pyrrolo[2,1-b][3]-benzazepine-11-one

2-Cyano-6,11-dihydro-5H-pyrrolo[2,1-b][3]benzazepin-11-one (222 mg.) and 222 mg. nickel-aluminum alloy in 2 ml. 75% formic acid is refluxed for 1½ hours. The solid is filtered off and washed with ethanol. The filtrate is diluted with 50 ml. water and extracted twice with 50 ml. methylene chloride. The organic layer is washed with water, 5% sodium bicarbonate and with water; it is then dried over magnesium sulfate and evaporated to dryness. Addition of ether induces crystallization and the crystals are filtered and air-dried to yield 125 mg. (56%) 2-formyl-6,11-dihydro-5H-pyrrolo[2,1-b][3]benzazepine-11-one, m.p. 135°–136° C.

EXAMPLE 4

2-Carbamoyl-6,11-dihydro-5H-pyrrolo[2,1-b][3]benzazepin-11-one

2-Cyano-6,11-dihydro-5H-pyrrolo[2,1-b][3]benzazepin-11-one (30 g., 0.135 mole) in 100 ml. of concentrated hydrochloric acid and 100 ml. of acetic acid was refluxed for 2 hours. It was then poured onto 500 ml. of water and continuously extracted with methylene chloride. The solution, from which crystals deposited during the extraction, was left to cool to room temperature and filtered to afford 2-carbamoyl-6,11-dihydro-11-oxo-5H-pyrrolo[2,1-b]-[3]benzazepine (27 g. 83%), m.p. 228° C.

EXAMPLE 5

6,11-Dihydro-11-oxo-5H-pyrrolo[2,1-b][3]benzazepine-2-carboxylic acid

To 2-carbamoyl-6,11-dihydro-pyrrolo[2,1-b][3]-benzazepine-11-one (27 g., 0.112 moles) in 300 ml. of 50% sulfuric acid maintained at 50° C., was added slowly 25 g. of sodium nitrite in 75 ml. of water. At the end of the addition, the solid was filtered, washed with water and air-dried to yield 6,11-dihydro-11-oxo-pyrrolo[2,1-b][3]-benzazepine-2-carboxylic acid (24 g., 89%), m.p. 287°-290° C.

EXAMPLE 6

2-Dimethylcarbamoyl-6,11-dihydro-5H-pyrrolo[2,1-b][3]-benzazepin-11-one

Step A: Preparation of 2-chlorocarbonyl-6,11-dihydro-5H-pyrrolo[2,1-b][3]benzazepin-11-one 6,11-Dihydro-11-oxo-pyrrolo[2,1-b][3]benzazepine-2-carboxylic acid (24 g., 99 mmoles) in 100 ml. of thionyl chloride was refluxed for 15 minutes. The volatiles were removed under vacuum and the residue was triturated in ether. Filtration and air-drying yielded 2-chlorocarbonyl-6,11-dihydro-5H-pyrrolo[2,1-b][3]benzazepin-11-one (23 g., 89%), m.p. 147°-148.5.

Step B: Preparation of 2-dimethylcarbamoyl-6,11-dihydro-5H-pyrrolo[2,1-b][3]benzazepine-11-one Anhydrous dimethylamine was bubbled through a suspension of 2-chlorocarbonyl-6,11-dihydro-5H-pyrrolo-[2,1-b][3]benzazepin-11-one (23 g., 88.5 mmoles) in 100 ml. of methylene chloride. (Note: the introduction of dimethylamine caused the mixture to reflux and this reflux stopped when all the acid chloride was reacted. This took about 1 hour and complete solution was obtained.)

The reaction mixture was washed with water and dried over sodium sulfate. It was then taken to dryness, triturated in ether, filtered and air-dried to yield 2-dimethylcarbamoyl-6,11-dihydro-5H-pyrrolo[2,1-b][3]benzazepin-11-one (20 g., 84%), m.p. 148°-149.5° C.

EXAMPLE 7

6,11-Dihydro-2-methoxycarbonyl-5H-pyrrolo[2,1-b][3]benzazepin-11-one 6,11-Dihydro-11-oxo-5H-pyrrolo[2,1-b][3]benzazepine-2-carboxylic acid (25.5 g., 0.11 moles) in 300 ml. of methanol saturated with hydrogen chloride was refluxed until a homogeneous solution was obtained (4 hours).

The volatiles were removed under vacuum and the residue was dissolved in 300 ml. of methylene chloride, washed with dilute sodium hydroxide and then with water. It was dried over sodium sulfate and concentrated. The residue was triturated in ether, filtered and air-dried, yielding 6,11-dihydro-2-methoxycarbonyl-5H-pyrrolo[2,1-b]-[3]benzazepin-11-one (23.5 g., 85%), m.p. 125°-127° C.

EXAMPLE 8

2-Trifluoromethylthio- and 3-trifluoromethylthio-6,11-dihydro-5H-pyrrolo[2,1-b][3]benzazepin-11-one 6,11-Dihydro-5H-pyrrolo[2,1-b][3]benzazepine-11-one (9.6 g., 48.7 mmoles) dissolved in pyridine (20 ml.) and chloroform (50 ml.) was treated with trifluoromethylsulfenyl chloride (12 g., 86.6 mmoles) in chloroform (50 ml.). The reaction mixture was left at room temperature for 2 hours.

The mixture was washed with water, dried over sodium sulfate and concentrated to 16.2 g. of a black oil.

This oil was adsorbed on 800 g. of silica gel. Elution with petroleum ether-ether 3:1 (v/v) yielded 3-trifluoromethylthio-6,11-dihydro-5H-pyrrolo[2,1-b][3]-benzazepine-11-one (8.4 g., 57.7%), m.p. 95°-95.5° C.

Elution with ether yielded 2-trifluoromethylthio-6,11-dihydro-5H-pyrrolo[2,1-b][3]benzazepine-11-one (4.2 g., 28.8%), m.p. 77°-78° C.

EXAMPLE 9

6,11-Dihydro-1-trifluoromethyl-(and -3-trifluoromethyl)-5H-pyrrolo[2,1-b][3]benzazepin-11-one A mixture of 8.9 g. of 6,11-dihydro-5H-pyrrolo[2,1-b][3]benzazepin-11-one, 30 of trifluoromethyl iodide, 20 ml. of pyridine and 300 ml. of acetonitrile was irradiated with a 450 watt lamp for 18 hours. The mixture was evaporated to dryness, and the residue was extracted with ether and filtered. The filtrate was evaporated to an oil. The oil was again treated with 25 g. of trifluoromethyl iodide in pyridine/acetonitrile and irradiated for 12 hours. Evaporation to dryness, extraction with ether, filtration and evaporation to dryness gave a crystalline residue. The residue was chromatographed on silica gel, by elution with benzene. Fraction 1 from the column provides 3.5 g. of product contaminated with traces of the 2-trifluoromethyl isomer. Fraction 2 provided 900 mg. of pure 6,11-dihydro-3-trifluoromethyl-5H-pyrrolo[2,1-b] [3]benzazepin-11-one, m.p. 90°-93° C.

Rechromatography of Fractions 3-5 provided pure 6,11-dihydro-1-trifluoromethyl-5H-pyrrolo[2,1-b][3]benzazepin-11-one, m.p. 102°-103° C.

Example 10

6,11-Dihydro-2-pentanoyl-5H-pyrrolo[2,1-b][3]benzazepin-11-one 6,11-Dihydro-5H-pyrrolo[2,1-b] [3]benzazepin-11-one (1.0 g.) was dissolved in 20 ml. of methylene chloride and 2.66 g. of aluminum chloride was added with cooling. At room temperature there was added little by little 720 mg. of pentanoyl chloride. Fifteen minutes after the addition was complete the mixture was poured onto ice. The organic phase was separated, filtered, dried and concentrated to dryness. The residue was triturated with ether, collected and dried to give 1.18 g. (85%) of 6,11-dihydro-2-pentanoyl-5H-pyrrolo[2,1-b] [3]benzazepin-11-one, m.p. 135°-136° C. Chromatography on silica gel by elution with benzene, and 5% (v/v) ethylacetate in benzene, raised the melting point to 137°-138° C.

Employing the procedure substantially as described in Example 10, but substituting for the pentanoyl chloride used therein, the acid chlorides described in Table V, there are produced the acyl-pyrrolobenzazepinones also described in Table V by the following procedure:

TABLE V

[Structure: benzazepinone with pyrrole] + XCl → [Structure: benzazepinone with pyrrole-X]

| X | product m.p. (° C.) |
|---|---|
| —C(=O)—CH₃ | 160–161 |
| —C(=O)—CH(CH₃)₂ | 124–126 |
| —SO₂N(CH₃)₂ [a] | 134–137 |

[a] reaction conducted in nitromethane at reflux temperature for 20 minutes.

Following the procedure of Example 10, but conducting the reaction at 100°–130° C. with excess alkanoyl chloride as solvent and without the aluminum chloride, there are produced mixtures of 2- and 3- alkanoyl ketones which upon chromatographic separation on silica gel provide the alkanoyl ketone products described in Table V and in Example 10 as well as the corresponding 3-pentanoyl-,3-acetyl-, and 3-isobutyroyl- compounds.

EXAMPLE 11

9-Iodo-6,11-dihydro-5H-pyrrolo[2,1-b] [3]benzazepin-11-one

Step A: Preparation of 7-nitro-3,4-dihydro-isocarbostyril

Fuming nitric acid (17 ml.) was added to 670 ml. of concentrated sulfuric acid at 0° C. 3,4-Dihydro-iso-carbostyril (50 g.) was added portionwise maintaining the temperature below 0° C. After 30 minutes at 0° C., the solution was poured into 8 l. of ice water. The crystalline precipitate is collected, washed with water and air dried to give 62.0 g. (95%) of 7-nitro-3,4-dihydroisocarbostyril, m.p. 225°–230° C. After recrystallization from acetone it has m.p. 230°–232° C.

Step B: Preparation of 7-amino-3,4-dihydro-isocarbostyril

The product from Step A (20 g.) was hydrogenated over 2.0 g. of 10% Pd/C in 350 ml. of methanol. The mixture was filtered, and the filtrate was evaporated to dryness. The residue was suspended in ether and collected on a filter to give 15.7 g. (93%) of 7-amino-3,4-dihydro-isocarbostyril, m.p. 123°–125° C.

Step C: Preparation of 7-iodo-3,4-dihydro-isocarbostyril

A solution of 690 mg. of sodium nitrite in 5 ml. of water was added dropwise to an ice-cold solution of 1.62 g. of 7-amino-3,4-dihydro-isocarbostyril in 4 ml. of concentrated hydrochloric acid and 12 ml. of water. After about 15 minutes at 0°–5° C. a solution of 1.7 g. of potassium iodide in 1 ml. of water was added and the mixture was allowed to warm to room temperature. Acetone (20 ml.) was added and the solution was held at room temperature for 1 hour and at 50°–60° C. for 1 hour. The mixture was concentrated to dryness. The residue was taken up in water, extracted with chloroform, the extract was dried and concentrated to dryness to give 2.0 g. (73%) of 7-iodo-3,4-dihydro-isocarbostyril.

Step D: Preparation of 2-aminoethyl-5-iodobenzoic acid hydrochloride

A mixture of 1.0 g. of 7-iodo compound from Step C and 40 ml. of concentrated hydrochloric acid was heated in a pressure vessel at 145° C. for 30 hours. The solution was concentrated to dryness. The residue was suspended in ether and collected to give 950 mg. (80%) of 2-aminoethyl-5-iodobenzoic acid hydrochloride, m.p. 200°–205° C.

Step E: Preparation of 2-(2-pyrrol-1-yl)ethyl-5-iodobenzoic acid

A mixture of 12.1 g. of product from Step D, 6.48 g. of 2,5-dimetoxytetrahydrofuran, 180 ml. of water and 30 ml. of acetic acid was stirred at 55° C. for 2 hours and at room temperature overnight. The mixture was diluted with water, extracted with chloroform, and the extract was extracted with 0.5% (w/v) sodium hydroxide solution. The alkaline extract was acidified with 6 N hydrochloric acid and extracted with chloroform. The extract was dried, filtered and concentrated to dryness. The oily residue was triturated with cyclohexane and the solids were collected to give 8.1 g. (58%) of 2-(2-pyrrol-1-yl)-ethyl-5-iodobenzoic acid, m.p. 92°–95° C.

Step F: Preparation of 9-iodo-6,11-dihydro-5H-pyrrolo-[2,1-b][3]benzazepin-11-one A mixture of 1 g. of the product from Step E and 20 ml. of polyphosphate ester was stirred 1.5 hrs. at room temperature. The mixture was cooled in ice and diluted with 75 ml. of water. The mixture was extracted with benzene and the extract was washed with water, dried and concentrated to dryness to give 500 mg. of 9-iodo-6,11-dihydro-5H-pyrrolo[2,1-b][3]benzazepin-11-one, which after recrystallization from cyclohexane had m.p. 120–122° C.

Following the procedure of Example 11, Steps C, D, E, and F but substituting for the potassium iodide used in Step C thereof an equimolecular amount of cuprous chloride, there is prepared 9-chloro-6,11-dihydro-5H-pyrrolo[2,1-b][3]benzazepin-11-one.

EXAMPLE 12

9-Trifluoromethylthio-6,11-dihydro-5H-pyrrolo[2,1-b][3]-benzazepin-11-one

A mixture of 2.4 g. of iodoketone (from Example 11), 5.14 g. of copper (electrolytic dust), 9.0 g. of bis(trifluoromethylthio)mercury and 20 ml. of dimethyl formamide was stirred and heated on a steam bath for 5 hours. The mixture was cooled in ice, treated with 75 ml. of benzene and treated dropwise with 50 ml. of 10% sodium hydroxide solution. After 1 hour at room temperature the mixture was filtered through diatomaceous earth followed by a benzene wash. The filtrate was extracted with benzene. The combined benzene fractions were washed with water, dried, filtered and concentrated to dryness to give 2.0 g. (90%) of 9-trifluoromethylthio-6,11-dihydro-5H-pyrrolo-[2,1-b][3]benzazepin-11-one, m.p. 81°-83° C.

Following the procedure of Example 12, but substituting for the copper dust and the bis(trifluoromethylthio) mercury used therein an equimolecular amount of cuprous methylsulfide or cuprous isopropylsulfide, there are produced 9-methylthio-6,11-dihydro-5H-pyrrolo[2,1-b]-[3]benzazepin-11-one, respectively.

EXAMPLE 13
9-Nitro-6,11-dihydro-5H-pyrrolo[2,1-b][3]benzazepin-11-one

Following the procedure of Example 11, Steps D, E, and F, but substituting for the 7-iodo-3,4-dihydroisocarbostyril used in Step D thereof, an equimolecular amount of 7-nitro3,4-dihydro-isocarbostyril, there is produced in sequence:

Step A: 2-aminoethyl-5-nitrobenzoic acid, m.p. 230°-232° C.;

Step B: 2-(2-pyrrol-1-yl)ethyl-5-nitrogenzoic acid, m.p. 147°-149° C.;

Step C:
9-nitro-6,11-dihydro-5H-pyrrolo[2,1-b][3]benzazepin-11-one, m.p. 190°-192° C.

EXAMPLE 14
9-Amino-6,11-Dihydro-5H-pyrrolo[2,1-b][3]benzazepin-11-one

Following the procedure of Example 11, Step B, but substituting for the 7-nitro-3,4-dihydro-isocarbostyril used therein an equimolecular amount of 9-nitro-6,11-dihydro-5H-pyrrolo [2,1-b][3]benzazepin-11-one, there is produced 9-amino-6,11 -dihydro-5H-pyrrolo[2,1-b][3]benzazepin- pin-11-one, m.p. 166°-167° C.

EXAMPLE 15
9-Methylamino-6,11-dihydro-5H-pyrrolo[2,1-b][3]benzazepin-11-one

A solution of 9amino-6,11-dihydro-5H-pyrrolo-[2,1-b][3]benzazepin-11-one in triethyl orthoformate (2.14 g.; 10 mmoles in 80 ml) is refluxed for 5 hours. The volatiles are removed under vacuum and the residue dissolved in 100 ml. of absolute ethanol is stirred in an ice bath as sodium borohydride (0.88 g.; 0.024 moles) is added over a period of 10 minutes. The mixture is stirred for a period of 2 hours. After concentration of the ethanol, the residue is dissolved in ethyl acetate, washed with water, dried over $Na_2SO_4$ and concentrated to dryness to yield 9-methylamino -6,11 -dihydro-5H-pyrrolo-[2,1-b][3]benzazepin-11-one.

EXAMPLE 16
9-Dimethylamino-6,11-dihydro-5H-pyrrolo[2,1-b][3]benzazepin-11-one To a solution of 9-amino-6,11-dihydro-5H-pyrrolo-[2,1-b][3]benzazepin-11-one (2.1 g., 10 mmoles) and 4 ml. (50 mmoles) of 37% aqueous formaldehyde in 15 ml. of acetonitrite is added 1 g. (16 mmoles) of sodium cyano borohydride. A vigorous and exothermic reaction takes place and a dark residue separates. The mixture is stirred for 15 minutes and then glacial acetic acid is added dropwise until the solution tests neutral on wet pH paper. Stirring is maintained for an additional 2 hours. The volatiles are removed under vacuum, and the residue is dissolved in chloroform. The solution is washed with base and with water, dried over sodium sulfate, and concentrated to leave a residue that is purified by chromatography on silica gel. Elution with chloroform yields 9-dimethylamino-6,11-dihydro-5H-pyrrolo [2,1-b][3]benzazepin-11one as a dark brown oil.

EXAMPLE 17
9-Cyano-6,11-dihydro-5H-pyrrolo[2,1-b][3]benzazepin-11-one

A stirred mixture of 1 gm. of 9-iodo-6,11-dihydro-5H-pyrrolo [2,1-b][3]benzazepin-11-one, 1 gm. of cuprous cyanide and 5 ml. of dimetnylformamide is heated to reflux for 5 hr. The mixture is then poured into a solution of 4 gm. of ferric chloride hydrate in 25 ml. of 2N hydrochloric acid. After stirring the resulting mixture at 60° for 30 min., it is extracted with 3 × 50 ml. of ethyl acetate, the organic extracts washed with 3 × 100 ml. of water and dried over $Na_2SO_4$. Evaporation of the dried solution yields 9-cyano-6,11dihydro-5H-pyrrolo- [2,1-b]- [3]benzazepin-11-one.

EXAMPLE 18
9-Trifluoromethylsulfinyl-6,11-dihydro-5H-purrolo[2,1-b]- [3]benzazepin-11-one A solution of 3 gm. of 9-trifluoromethylthio- 6,11-dihydro-5H-pyrrolo[2,1-b][3]benzazepin-11-one in 25 ml. of acetic acid containing 3 ml. of 50% hydrogen peroxide is stirred at 25° C. for 6 hr. The solvent is evaporated and the residue dissolved in 100 ml. of methylene chloride. The solution is washed with 2 × 25 ml. of 5% $Na_2CO_3$ solution, dried and evaporated. Chromatography of the residue on silica gel yields 9-trifluoromethylsulfinyl-6,11- dihydro-5H-pyrrolo [2,1-b][3]benzazepin-11-one.

Employing the procedure of Example 18, but substituting for the 9-trifluoromethylthio-6,11-dihydro-5H-benzazepin-11-one used therein, an equimolecular amount of the corresponding 9methylthio- or 9-isopropylthio- compounds, there are produced respectively 9-methylsulfinyl- 6,11 -dihydro-5H-pyrrolo[2,1-b][3]benzazepin-11-one and 9- isopropylsulfinyl-6,11 -dihydro-5H-pyrrolo[2,1-b][3]benzazepin-11-one.

EXAMPLE 19
9-Trifluoromethylsulfonyl-6,11-dihydro-5H-pyrrolo[2,1-b]- [3]benzazepin-11-one A solution of 2 gm. of 9-trifluoromethylsulfinyl- 6,11 -dihydro-5H-pyrrolo[2,1-b][3]benzazepin-11-one in 20 ml. of acetic acid containing 5 ml. of 90% hydrogen peroxide is stirred at 25° C. for 4 days. The solvent is evaporated and the residue dissolved in 100 ml. of methylene chloride. After washing the organic solution with 2 × 25 ml. of 1N $Na_2CO_3$, it is dried and evaporated, and the residue chromatographed on silica gel to yield 9-trifluoro- methylsulfonly-6,11-dihydro-5H-pyrrolo[2,1-b][3]benzazepin- 11-one.

Employing the procedure of Example 18, but substituting for the 9-trifluoromethylthio-6,11-dihydro-5H-pyrrolo[2,1-b][3]benzazepin-11-one used therein, an equimolecular amount of the corresponding 9-methylthio- or 9- isopropylthio- compounds, there are produced respectively 9-methylsulfonyl-6,11-dihydro-5H-pyrrolo[2,1-b][3]-benzazepin-11-one and 9-isopropylsulfonyl -6,11-dihydro-5H-pyrrolo[2,1-b][3]benzazepin-11-one.

EXAMPLE 20

9-Formyl-6,11-dihydro-5H-pyrrolo[2,1-b][3]benzazepin-11-one

Employing the procedure of Example 3 but substituting for the 2-cyano compound used therein, an equimolecular amount of 9-cyano-6,11-dihydro-5H-pyrrolo[2,1-b][3]benzazepine there is produced 9-formyl-6,11-dihydro-5H-pyrrolo[2,1-b][3]benzazepin-11-one.

EXAMPLE 21

9-Trifluoromethyl-6,11-dihydro-5H-pyrrolo[2,1-b][3]-benzazepin 11-one

A mixture of 5 g. of the 9-iodo ketone, 25 g. of trifluoromethyl iodide, 9 g. of precipitated copper and 150 ml. of dimethylformamide is heated in a stainless steel tube with shaking for 12 hr. at 140° C. Work-up of the reaction mixture and chromatography yield the title compound.

What is claimed is:

1. A compound of structural formula:

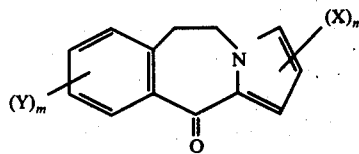

wherein $n$ is [3, 2, ]1, or 0 (X is hydrogen);
$m$ is [4, 3, 2,[1 or 0 (Y is hydrogen); and
X and Y are independently selected from
(1) hydrogen,
(2) halo,
(3) formyl,
(4) lower alkanoyl,
(5) lower alkyl,
(6) lower alkoxycarbonyl,
(7) hydroxy-lower alkyl,
(8) perhalo-lower alkyl,
(9) lower alkoxy,
(10) cyano,
(11) perhalo-lower alkylthio,
(12) lower alkylthio,
(13) lower alkylsulfonyl,
(14) perhalo-lower alkylsulfonyl,
(15) lower alkylsulfinyl,
(16) perhalo-alkylsulfinyl,
(17) amino,
(18) lower alkanoylamino,
(19) lower alkylamino,
(20) di(lower alkyl)amino,
(21) hydroxy,
(22) N-lower alkylcarbamoyl,
(23) N,N-di(lower alkyl)carbamoyl,
(24) nitro,
(25) di(lower alkyl)sulfamoyl,
(26) lower alkoxycarbonylamino,
(27) N-loweralkyl-carbamoyloxy,
(28) carboxy, and
(29) carbamoyl;
with the proviso that if $m$ is 0 (Y is hydrogen), $n$ is 1 and X is —CN, X is in the 2 or 3-position.

2. 2,3-Dichloro-6,11-dihydro-5H-pyrrolo[2,1-b][3]benzazepin-11-one.

3. The compound of claim 1 of structural formula:

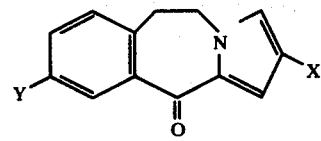

wherein X and Y are as defined therein.

4. The compound of claim 3, wherein one of X and Y is hydrogen and the other is hydrogen, cyano, or $C_{2-6}$ alkanoyl.

5. The compound of claim 4 which is 6,11-dihydro-5H-pyrrolo[2,1-b][3]benzazepin-11-one.

6. The compound of claim 4 which is 2-cyano-6,11-dihydro-5H-pyrrolo[2,1-b][3]benzazepin-11-one.

7. The compound of claim 4 which is 2-pentanoyl-6,11-dihydro-5H-pyrrolo[2,1-b][3]benzazepin-11-one.

8. 9-Chloro-6,11-dihydro-5H-pyrrolo[2,1-b][3]benzazepin-11-one.

9. 2,3-Dibromo-6,11-dihydro-5H-pyrrolo[2,1-b][3]benzazepin-11-one.

10. 2,3-Dibromo-9-N-methylcarbamoyloxy-6,11-dihydro-5H-pyrrolo[2,1-b][3]benzazepin-11-one.

11. 2,3-Dibromo-9-methoxycarbonylamino-6,11-dihydro-5H-pyrrolo[2,1-b][3]benzazepin-11-one.

12. 2,3-Dibromo-9-methyl-6,11-dihydro-5H-pyrrolo[2,1-b][3]benzazepin-11-one.

13. 1,2,3-Tribromo-6,11-dihydro-5H-pyrrolo[2,1-b][3]benzazepin-11-one.

14. 1,3-Dibromo-2-methyl-6,11-dihydro-5H-pyrrolo[2,1-b][3]benzazepin-11-one.

15. 1,2,3-Tribromo-9-acetylamino-6,11-dihydro-5H-pyrrolo[2,1-b][3]benzazepin-11-one.

16. 2,3-Dibromo-9-isopropyl-6,11-dihydro-5H-pyrrolo[2,1-b][3]benzazepin-11-one.

17. 2,3-Dibromo-9-metylthio-6,11-dihydro-5H-pyrrolo [2,1-b][3]benzazepin-11-one.

18. 2-Cyano-8,9-dimethyl-6,11-dihydro-5H-pyrrolo [2,1-b]benzazepin-11-one.

* * * * *

UNITED STATES PATENT OFFICE
CERTIFICATE OF CORRECTION

Patent No. 4,075,225   Dated February 21, 1978

Inventor(s) Joshua Rokach et al.

It is certified that error appears in the above-identified patent and that said Letters Patent are hereby corrected as shown below:

Claim 1, column 17, line 32; "n is [3,2,]1, or 0 (X is hydrogen); should be --- n is 1, or 0 (X is hydrogen); ---

Claim 1, column 17, line 33; "m is [4,3,2,[1 or 0 (Y is hydrogen); and" should be --- m is 1 or 0 (Y is hydrogen); and ---.

Signed and Sealed this

Twenty-seventh Day of June 1978

[SEAL]

Attest:

RUTH C. MASON
Attesting Officer

DONALD W. BANNER
Commissioner of Patents and Trademarks